(12) United States Patent
Antignano

(10) Patent No.: US 8,708,698 B2
(45) Date of Patent: Apr. 29, 2014

(54) LIGATING DEVICE FOR ARCH WIRES OR ORTHODONTIC WIRES AND RESPECTIVE METHOD FOR THE APPLICATION OF AN ARCH WIRE OR AN ORTHODONTIC WIRE

(75) Inventor: Giuseppe Antignano, Rocca d'Evandro (IT)

(73) Assignee: Orthodontic Manufacturer SIA S.R.L., Rocca d'Evandro (CE) (IT)

( * ) Notice: Subject to any disclaimer, the term of this patent is extended or adjusted under 35 U.S.C. 154(b) by 0 days.

(21) Appl. No.: 13/115,934

(22) Filed: May 25, 2011

(65) Prior Publication Data
US 2011/0300501 A1 Dec. 8, 2011

(30) Foreign Application Priority Data
Jun. 4, 2010 (IT) .............................. RM2010A0303

(51) Int. Cl.
*A61C 7/34* (2006.01)
(52) U.S. Cl.
USPC ........................................................ 433/14

(58) Field of Classification Search
USPC .............................................. 433/8–14, 15, 16
See application file for complete search history.

(56) References Cited

U.S. PATENT DOCUMENTS

| | | | | |
|---|---|---|---|---|
| 4,209,906 | A * | 7/1980 | Fujita | 433/11 |
| 4,355,975 | A * | 10/1982 | Fujita | 433/11 |
| 6,190,166 | B1 * | 2/2001 | Sasakura | 433/14 |
| 7,118,373 | B2 * | 10/2006 | Abels et al. | 433/8 |
| 2006/0019212 | A1 * | 1/2006 | Macchi | 433/14 |
| 2006/0228664 | A1 * | 10/2006 | Castner et al. | 433/11 |
| 2007/0248928 | A1 * | 10/2007 | Damon | 433/10 |

* cited by examiner

*Primary Examiner* — Cris L Rodriguez
*Assistant Examiner* — Matthew Seward
(74) *Attorney, Agent, or Firm* — Mark M. Friedman

(57) ABSTRACT

The present invention relates to a ligating device (1) for arch wires or orthodontic wires, having a bondable base (2), for coupling to a tooth, and a main body (3), where the main body (3) has a slot (4), suitable for receiving a metal arch wire (5). The slot (4) has its entrance on one of its gingival or occlusal sides. The invention relates also to a method for the application of an arch wire or an orthodontic wire (5), by insertion of the arch wire or orthodontic wire (5) in a plurality of ligating devices (1) for arch wires or orthodontic wires, along a gingival-occlusal, or occlusal-gingival direction of insertion.

11 Claims, 15 Drawing Sheets

LIGATING DEVICE FOR ARCH WIRES OR ORTHODONTIC WIRES AND RESPECTIVE METHOD FOR THE APPLICATION OF AN ARCH WIRE OR AN ORTHODONTIC WIRE

The present invention relates a ligating device for arch wires or orthodontic wires.

The invention concerns also a method for the application of an arch wire or an orthodontic wire.

In particular, the invention concerns a device of the said type with reduced dimensions, that allows inserting an arch wire or an orthodontic wire along the gingival-occlusal or occlusal-gingival direction and, more in detail, a device of the said type that allows using an arch wire with a rectangular cross section oriented with the longest side of its section along the gingival-occlusal direction.

The need to fit an orthodontic appliance on one's own teeth fixed, for aesthetic or even often for health reasons, involves having to stick, to each tooth to be treated, a ligating device to a metal arch wire or orthodontic wire. The arch wire tends to remain in his own position, not adapting to that of the ligating devices, then it forces the latter to rotate, and consequently also the teeth, to which those ligating devices are glued, rotate to align along the arc. Such devices, although effective, lead to the annoyance of having to stand, for a period of time that sometimes may exceed a year, the presence of foreign objects on the surface of one's own teeth.

Over the years the orthodontic technique has developed ligating devices smaller and smaller, so as to minimize the discomfort to the patient, as well as the aesthetic impact on it, but there is a volume that can not be reduced, i.e. the one of the metal arch wire itself. Nowadays "self-ligating devices of the passive type" are defined as the ligating devices that are not able to tighten the arch wire on the bottom of the slot without an external fastening device. Instead, "self-ligating devices of active type" are defined as the ligating devices which are able to press the wire on the bottom of the slot. Consequently the active stage of the system is defined the stage in which the ligating devices transfer the torque to the teeth.

For the time being, then before the present invention, during the active stage of the treatment of the teeth, an arch wire with a rectangular cross section is used, and in such stage the arch wire or orthodontic wire is pressed into the slot so as it transfers the torque; the section of this arch wire is oriented with it longest side along the lingual-vestibular direction, so as a greater resistance to bending is gained and, then, a greater force on the ligating devices and consequently on the teeth to be treated is applied.

Then a need is evident, i.e. to realize a ligating device of the said type that allows using an arch wire with a rectangular section, oriented with its longest side along the gingival-occlusal direction, in order to further reduce the volume of the ligating device along the vestibular-lingual direction. Such system exerts on said arch wire a force enough to obtain at least the same results that known ligating devices obtain.

It is then object of the present invention to overcome the above drawbacks, providing a ligating device of the said type that allows using an arch wire with a rectangular section, oriented with the longest side of its section along the gingival-occlusal direction, in order to further reduce the volume of the ligating device along the vestibular-lingual direction.

It is a further object of the present invention to provide a ligating device of the said type, which exerts on the arch wire, inserted in the latter, a force enough to obtain at least the same results that known ligating devices obtain.

It is another object of the present invention to realize a device of the said type which is usable even in the passive stage of the treatment, as previously described, during which an arch wire or an orthodontic wire with a round section is not pressed in the slot, but it has to slide into it with as less friction as possible.

Finally, it is an object of the present invention to realize a device of the said type, that is safe and reliable, that allows an easy realizing and is competitive in the market.

It is therefore the specific subject-matter of the present invention a ligating device for arch wires or orthodontic wires, comprising a comprising a bondable base, for coupling to the tooth, and a main body, said main body having a slot, suitable for receiving a metal arch wire or orthodontic wire, said device being characterized in that said slot has its entrance on one of its gingival or occlusal sides.

According to the invention, said slot is made accessible/closable by a clip, said body has, on the plane parallel to the tooth on which it is installed, an opening, suitable for receiving said clip, and said clip opens and closes said slot sliding along a vestibular-lingual axis.

Furthermore, according to the invention, said slot, in case said arch wire has a substantially rectangular section, is shaped such as to receive said arch wire with the longest side of its section oriented along the gingival-occlusal direction.

Preferably, according to the invention, said slot has a tilt from the gingival-occlusal axis, of an angle comprised between −25° and +25°.

Again, according to the invention, said body has a section substantially "U"-shaped, defining on both sides of said slot a first lingual arm and a second vestibular arm.

Still according to the invention, said body has, on the side opposite to said entrance of said slot, tiewings.

Still according to the invention, said body has, on its gingival side, one or more hooks.

According to the invention, moreover, said clip is substantially "U"-shaped, having one first arm towards to said entrance of said slot and a second arm opposite to said first arm.

Besides, according to the invention, said second arm of said clip has a first slit, determining two flaps, each provided with an obstacle, next to its free end, and said opening has, along one of its sides, opposite to said entrance of said slot, in central position, a protrusion, suitable for guiding the sliding of said clip along said first slit, and for stop it close to said obstacles, such as the same said clip does not come out from said body.

Preferably, according to the invention, said first arm of said clip has a second slit, determining two flaps, and in that said opening has, at the end of one of its sides, gingival or occlusal, two grooves, suitable for receiving said flaps in one opening and/or closing stage of said device.

Again, according to the invention, said flaps have a shape protruding toward outside from the total volume of said clip.

Still according to the invention, said grooves have external inclined walls, suitable for facilitating the introduction of said clip with the only pressure of the fingers of a user, and for preventing its coming out in the absence of an external force.

Preferably, the invention provides the use of an external tool, equipped with a handle and a tip, suitable for coupling itself with said first slit, such as to exert on said clip a force in the lingual-vestibular direction, enough to make said slot move from a closed position to an open position.

It is a further subject-matter of the present invention a method for the application of an arch wire or an orthodontic wire, characterized in providing the insertion of said arch wire or orthodontic wire in a plurality of ligating devices for arch wires or orthodontic wires, along a gingival-occlusal, or occlusal-gingival, direction of insertion, of said plurality of devices.

Further, according to the invention, said arch wire or orthodontic wire has a substantially rectangular section, and it is provided the insertion of said arch wire or orthodontic wire in said plurality of devices with the longest side of its section oriented along the gingival-occlusal direction.

Finally, the invention it provides the installation of said plurality of devices on a respective plurality of teeth, said devices being oriented, alternately, in groups of single teeth or more teeth, such as having the entrance for said arch wire or orthodontic wire on a gingival side and/or an occlusal side.

The present invention will be now described, by way of illustration but not by way of limitation, with particular reference to the figures of the enclosed drawings, wherein the operation of the device according to the invention is schematically shown. In particular, FIG. 1 shows in (a) a schematical side view of a first embodiment of a device according to the invention, oriented with the entrance for the arch wire along a gingival direction, in (b) a schematical side view of a second embodiment of a device according to the invention, oriented with the entrance for the arch wire along a gingival direction, in (c) a schematical side view of the device of FIG. 1b, oriented with the entrance for the arch wire along a occlusal direction;

In the description of the different figures, the orientation of the different elements will be referred to the device according to the invention applied to a tooth.

Figure 1A:
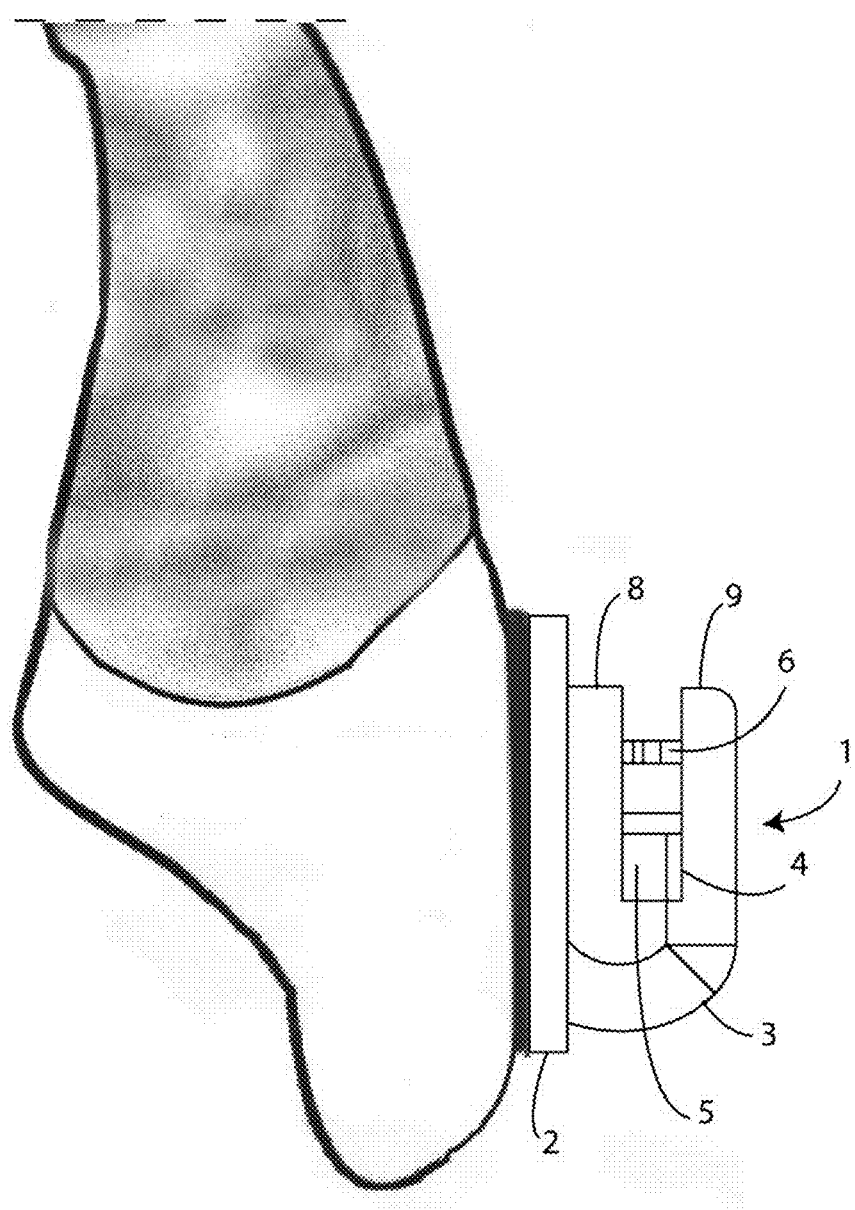
Figure 1B:
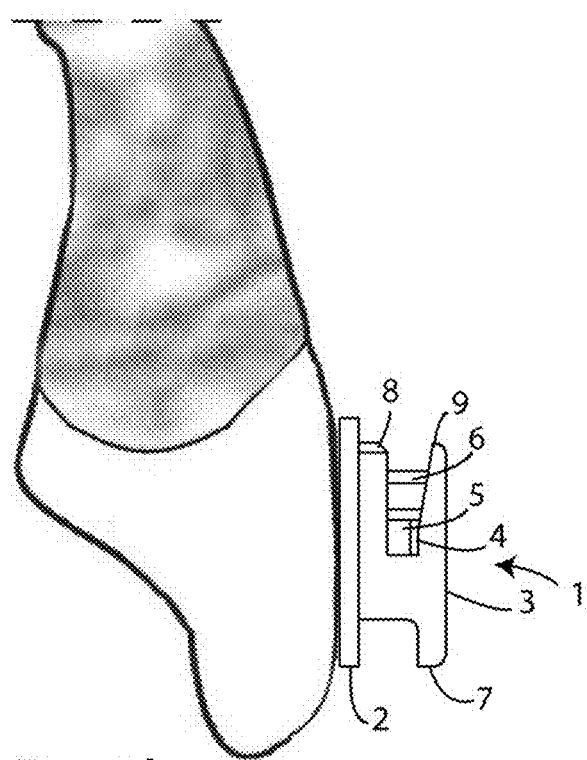
Figure 2:
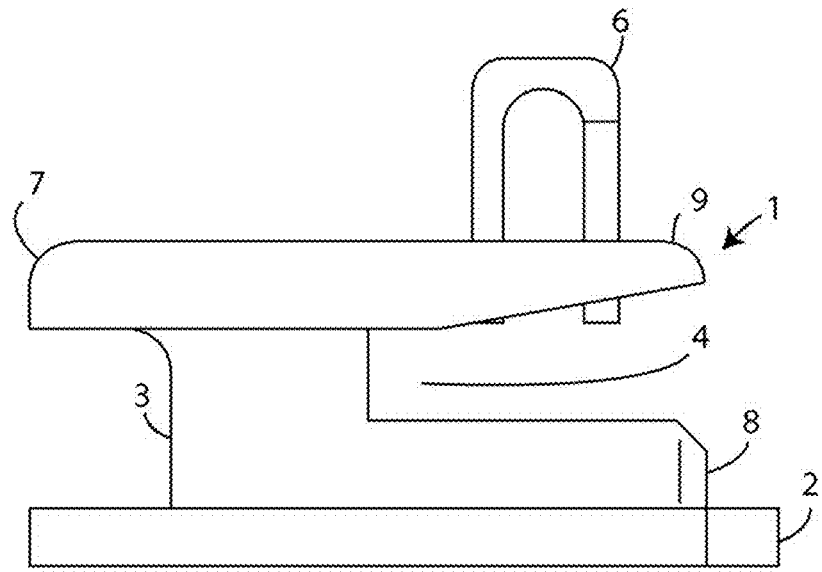
FIG. 2 is a side view of the device of FIGS. 1b and 1c, with closing clip in opening position.
Figure 3:
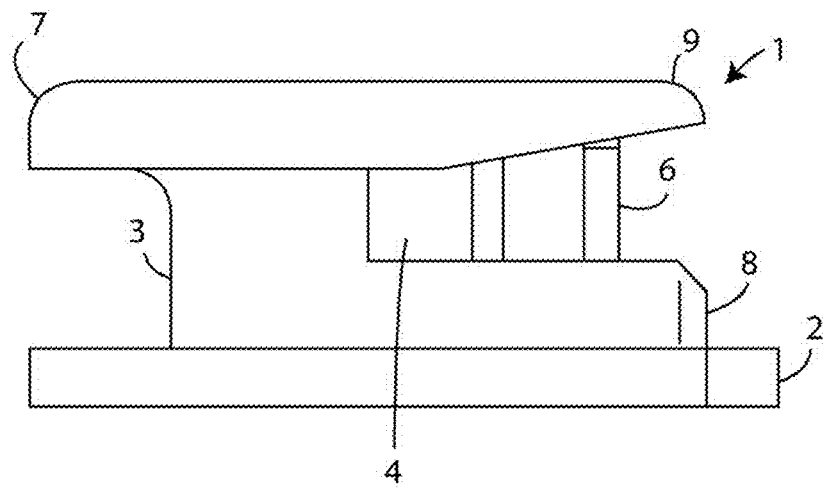
FIG. 3 is a side view of the device of FIGS. 1b and 1c, with closing clip in closing position.

Observing at first FIGS. 1, 2 and 3 of the enclosed drawings, the ligating device, marked with the general reference number 1, comprises a bondable base 2, for coupling to the tooth, and a main body 3, which has a slot 4, (in the following called also slot) suitable for receiving a metal arch wire 5, that can be opened/closed by means of a clip 6.

The main body 3 can have different shapes, i.e. the one represented in FIG. 1a, having a section substantially "U"-shaped, but it is to be understood that this basic shapes may alternate with other ones, i.e. that shown in FIGS. 1b and 1c, with the ancillary presence of wings (in the following called also "tie-wings") 7.

Figure 1C:
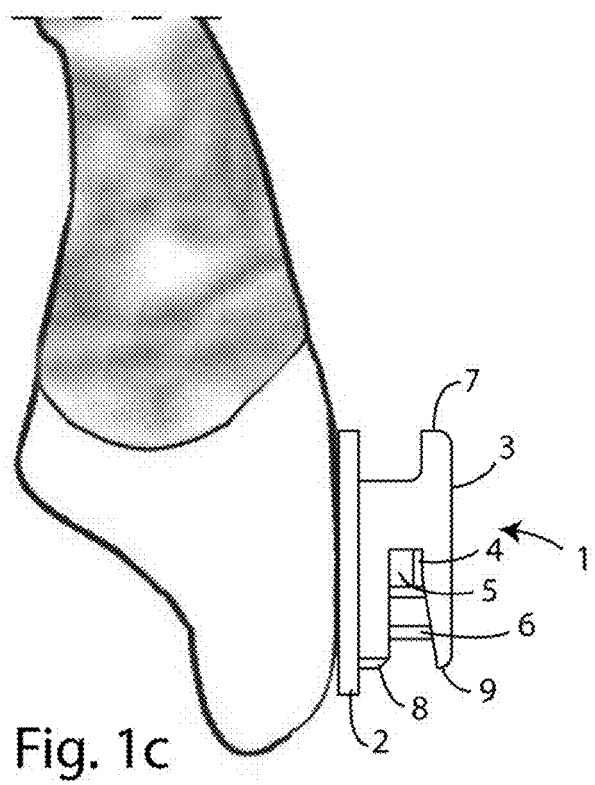

Anyway, the substantially "U"-shaped conformation of the main body 3, and its orientation in respect with the tooth, allow inserting said arch wire 5 inside it along the gingival-occlusal direction, with its entrance for the arch wire on its gingival side (FIGS. 1a, 1b) or on its occlusal side (FIG. 1c). Furthermore, as a benefit, the device can be applied with alternate orientation on each tooth, (i.e. on a canine with the entrance on the occlusal side and on the adjacent premolar with the entrance on the gingival side), or on groups of adjacent teeth (i.e. on a first group of two or more adjacent teeth with the entrance on the occlusal side, and on a second group, adjacent to the first one, with the entrance on the gingival side), in order to facilitate the arch reaching the end of the slot 4. Still, advantageously, it is possible to apply a plurality of devices, subject-matter of the present invention, all of those on the upper dental arch having a gingival orientation and all of those on the lower dental arch having an occlusal orientation, or vice versa. This makes harder for the arch wire to come out from the device, with respect to the traditional ligating devices, that require the inserting along the vestibular-lingual direction, even when the clip 6 is in the opening position. In such a way the dentist has a an easier control on his work.

As is evident from the figures, the slot 4 is shaped in order to receive an arch wire 5, with any section, (see also FIGS. 11a and 11b), acting both as an active device and a passive one. In case of an arch wire 5 with rectangular section (as shown in FIG. 1), it is oriented with the longest side of its section along the gingival-occlusal direction.

In particular, in the enclosed figures a slot 4 with a substantially rectangular section is shown. In this case, the slot 4 can have a tilt, of an angle comprised between −25° and 25°, (FIGS. 13 and 14) to correct an incidental rotation of a tooth.

Said body 3, with a "U"-shaped section, has a lingual arm 8 and a vestibular arm 9.

Figure 4A:
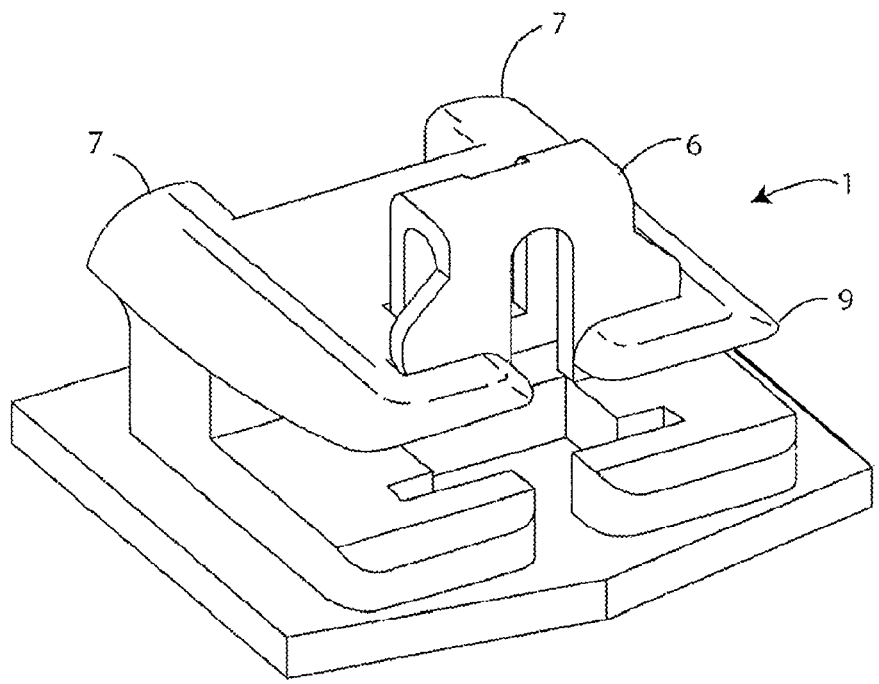
FIGS. 4a and 4b are perspective views of the device of FIGS. 1b and 1c, respectively with clip in opening and closing position.
Figure 4B:
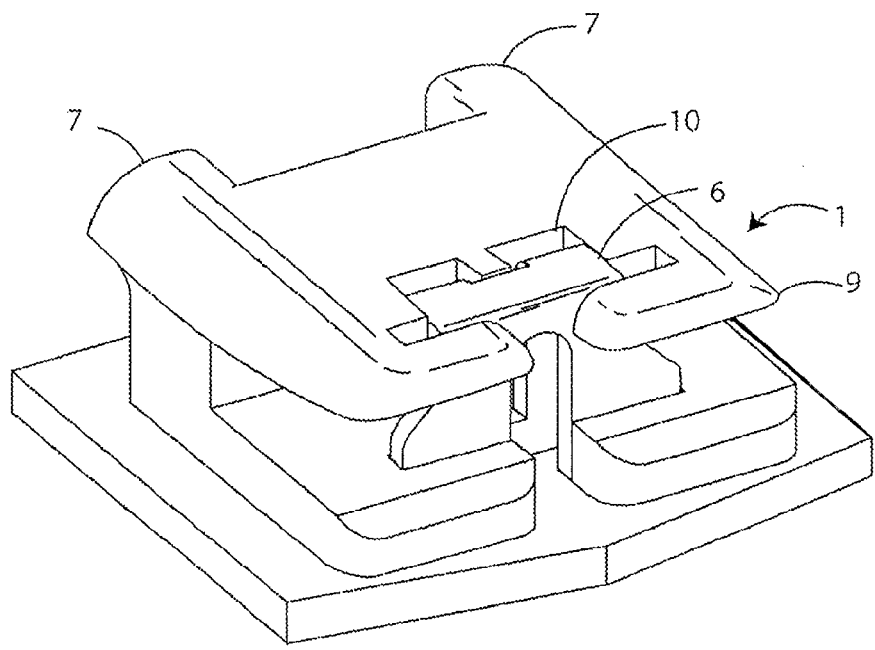

Observing now FIGS. 4, 5 and 6, the body 3 has, on the plane parallel to the tooth on which it is installed, a substantially "C"-shaped section, determining an opening 10 through both arms 8, 9, lingual and vestibular, which is suitable for receiving the clip 6 and to allow its sliding along the lingual-vestibular direction and vice versa, moving from an opening position (FIG. 4a) and a closing position (FIG. 4b).

Figure 6A:
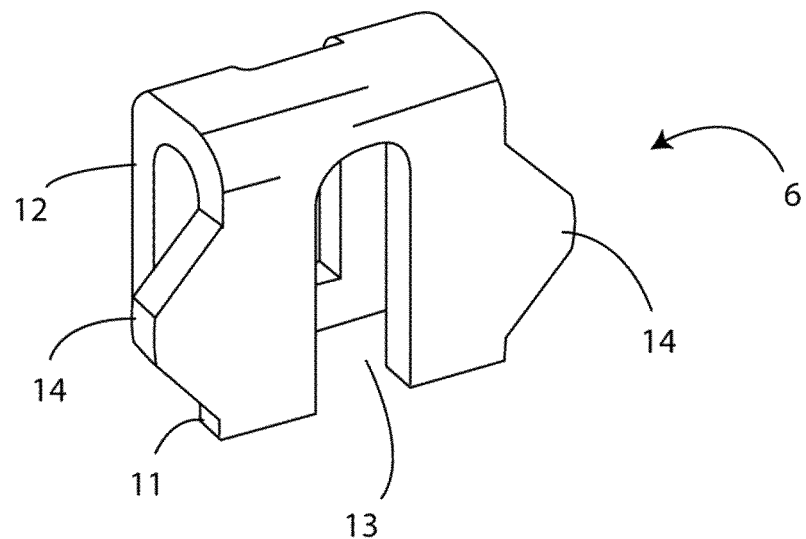
FIGS. 6a and 6b show, respectively in a view towards the entrance for the arch wire and in a view towards the opposite side, the closing clip of the device according to the invention.
Figure 6B:
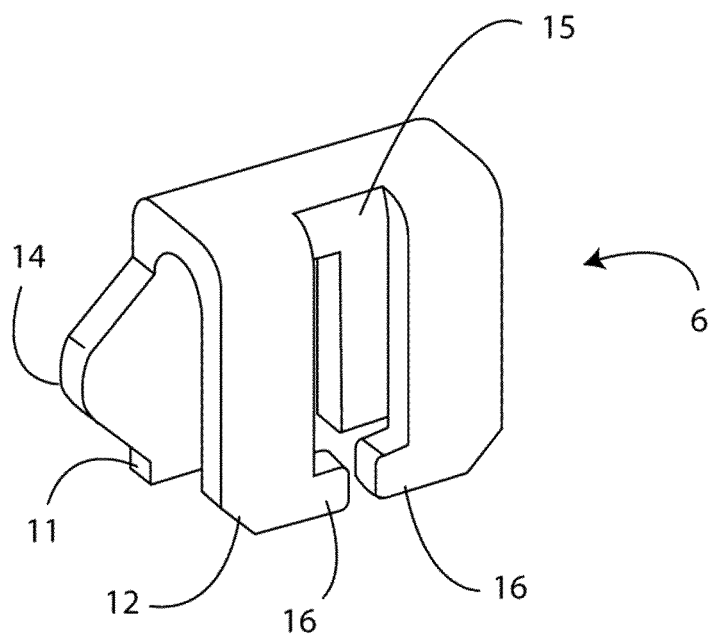

In FIGS. 6a and 6b the clip 6 is shown, substantially "U"-shaped, having one arm 11 towards to the entrance of the slot 4 and an opposite arm 12.

The arm 11 of the clip 6 has a slit 13, determining two flaps 14, with a shape protruding toward outside from the total volume of the clip 6; the arm 12 of the clip 6 has a slit 15, determining two flaps, each with an obstacle 16, next to its free end.

Figure 6C:
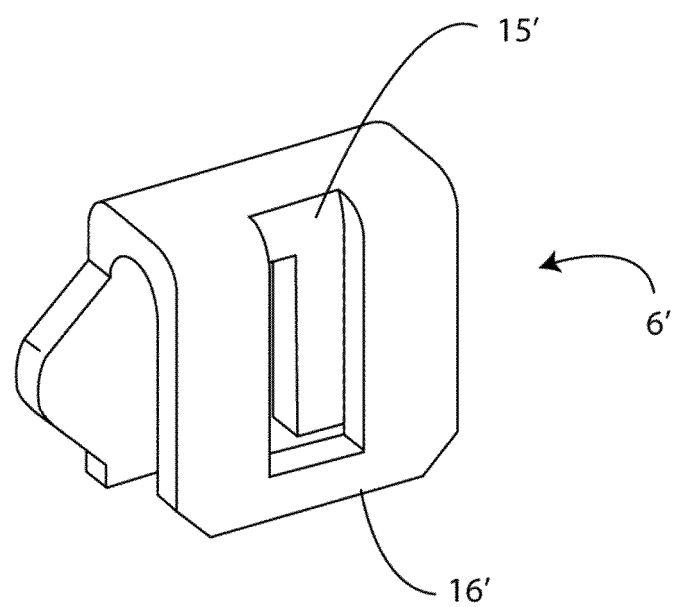
FIG. 6c shows, in a view towards the opposite side to the entrance for the arch wire, a further embodiment of the closing clip of the device according to the invention.

According to a further embodiment, in FIG. 6c a clip 6' is shown, with a slit 15', determining two flaps, the obstacle 16' of which are joint together, realizing a single obstacle.

Figure 5A:
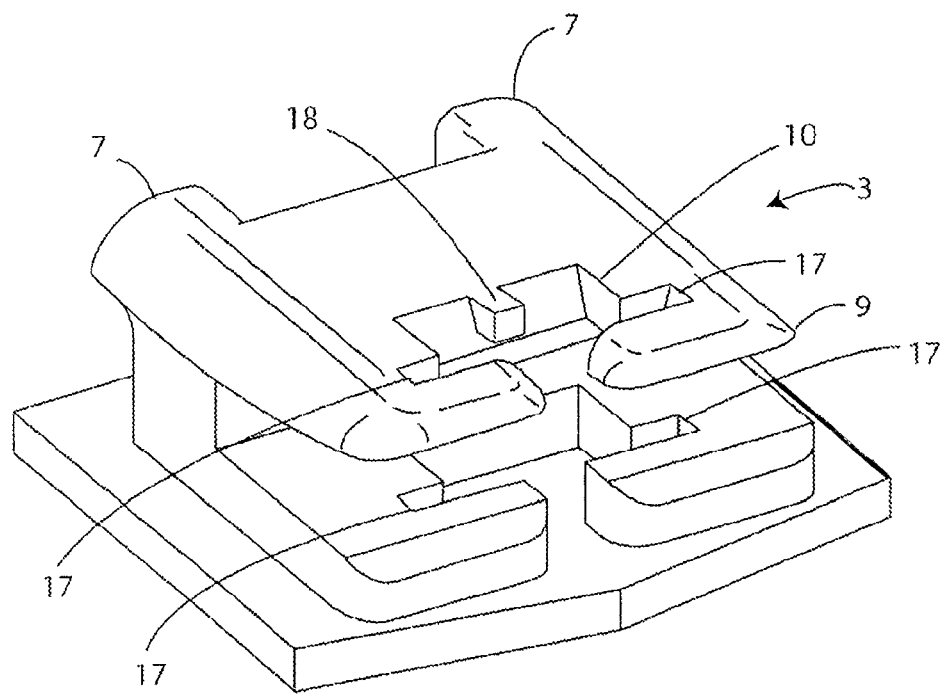
FIGS. 5a and 5b show a perspective view, respectively of the device of FIGS. 1b and 1c, and of the device of FIG. 1a, wherein the closing clip has been removed.
Figure 5B:
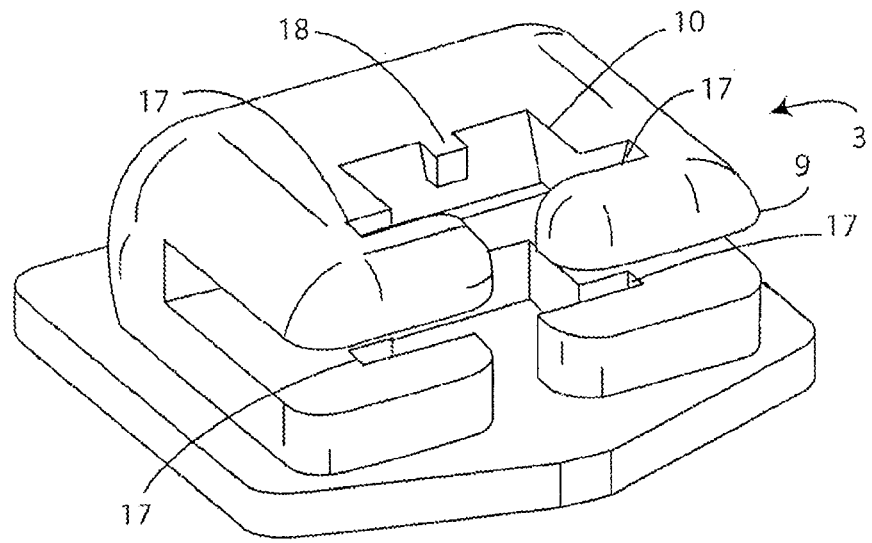

In FIGS. 5a and 5b the opening 10 can be seen, respectively in case of the device of FIGS. 1b and 1c, and in case of FIG. 1a.

Such opening 10 has at the end of one of its sides, corresponding to the entrance for the arch wire, two grooves 17, in both arms 8, 9, lingual and vestibular, suitable for receiving said flaps 14 of the arm 11 of the clip 6 in one opening and/or closing stage of the device 1 according to the invention.

On the vestibular arm 9 of the body 3, along the occlusal side of the opening 10, in central position, there is a protrusion 18.

Figure 7A:
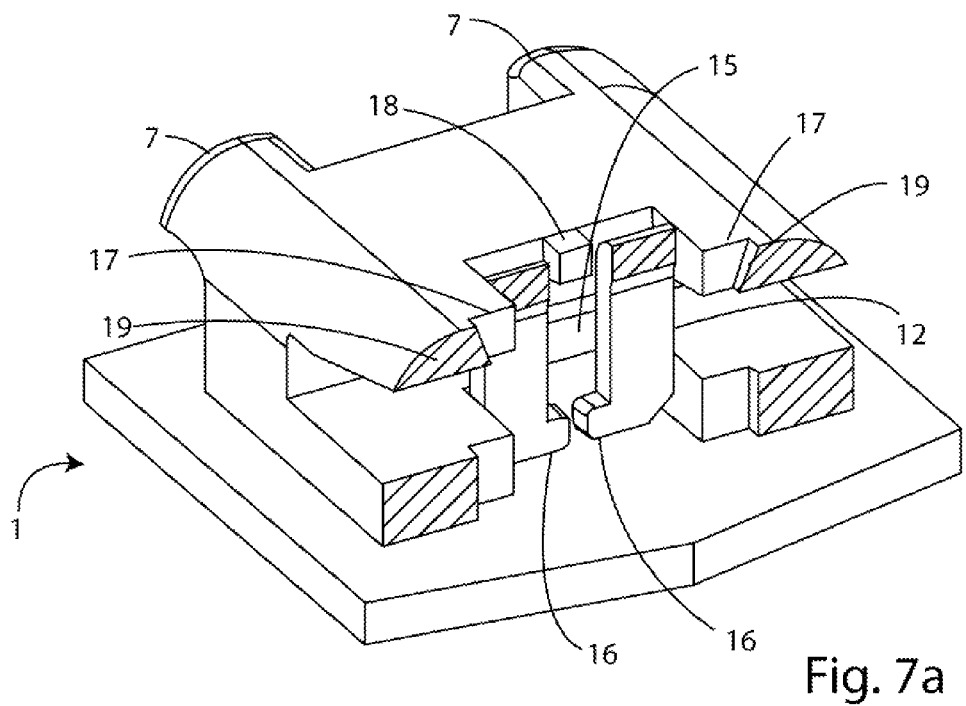
FIGS. 7a and 7b are perspective views, with elements in a vertical section, and the closing clip in a cross section, of the device according to the invention, in an open and closed positions.
Figure 7B:
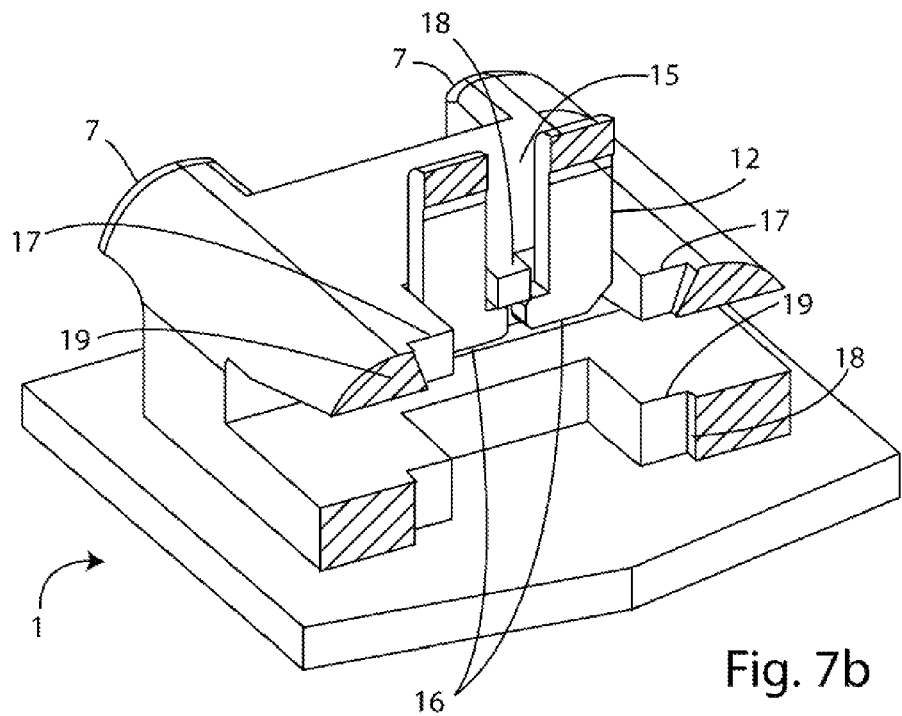

Observing now FIG. 7, it is noticed that the protrusion 18 is suitable for guiding the sliding of the clip 6 along the slit 15 of the arm 12, so as the same clip 6 does not come out from the body 3, avoiding that it is lost in the mouth of the patient.

Figure 8A:
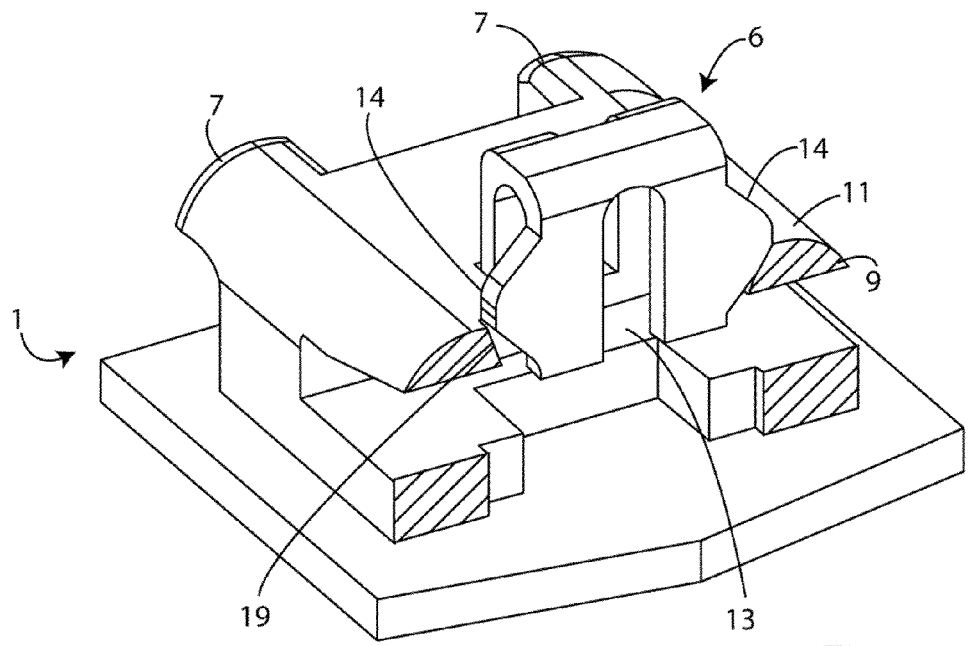
FIGS. 8a and 8b are perspective views, with elements in a vertical section, and the closing clip not sectioned, of the device according to the invention, in an open and closed positions.
Figure 8B:
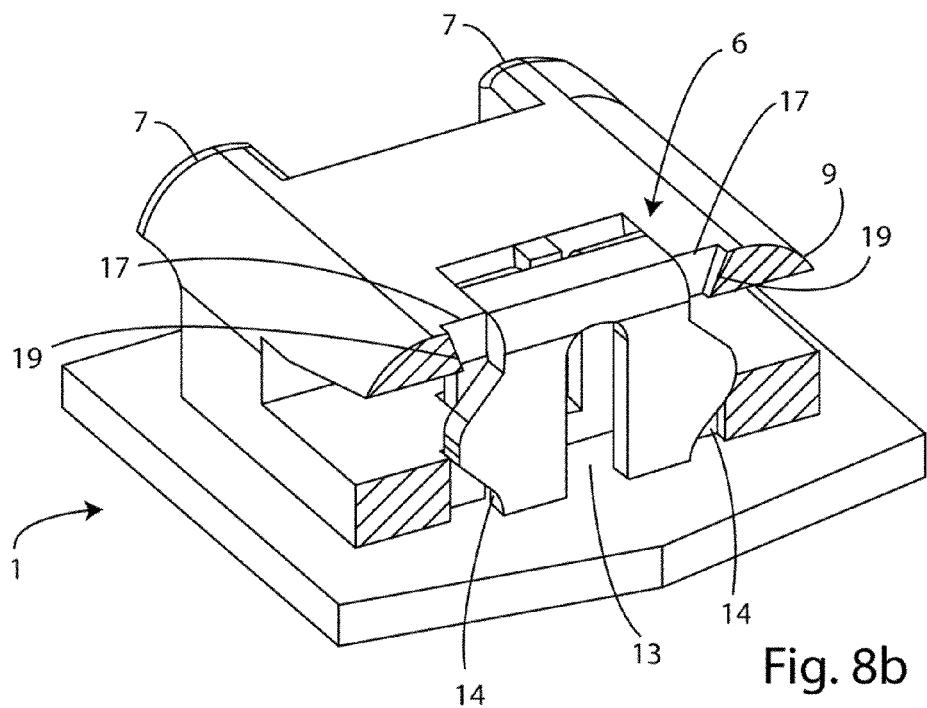

As it is clear from FIG. 8, the flaps 14, on the arm 11 of the clip 6, have a curved shape, with a central protrusion, substantially semicircular. The shape of the flaps 14 is such as it is not able to pass through the grooves 17, both in the opening position (FIGS. 4a, 8a), and in the closing position (FIGS. 4b, 8b), unless a force is exerted on the clip 6. Indeed, in order to move from the opening position to the closing position, a pressure along the vestibular-lingual direction is necessary, and vice versa. The pressure exerted on the clip towards the grooves 17, on the vestibular arm 9 of the body 3, that is the arm to be crossed, make the flaps 14 get closer to each other, compressing the slit 13, during the passage through the grooves 17 on the vestibular arm 9. Once the flaps 14 have gone beyond the grooves 17, the slit 13 goes back in the rest position, and the flaps 14 are housed into the grooves 17 in a closing position, or outside the body 3, in an opening position.

The grooves 17 of the arm 9 have inclined walls 19 which facilitate the introduction of the clip with the only pressure of the fingers (not shown in the figure) of a user, and that prevent its coming out in the absence of an external force.

Figure 9A:
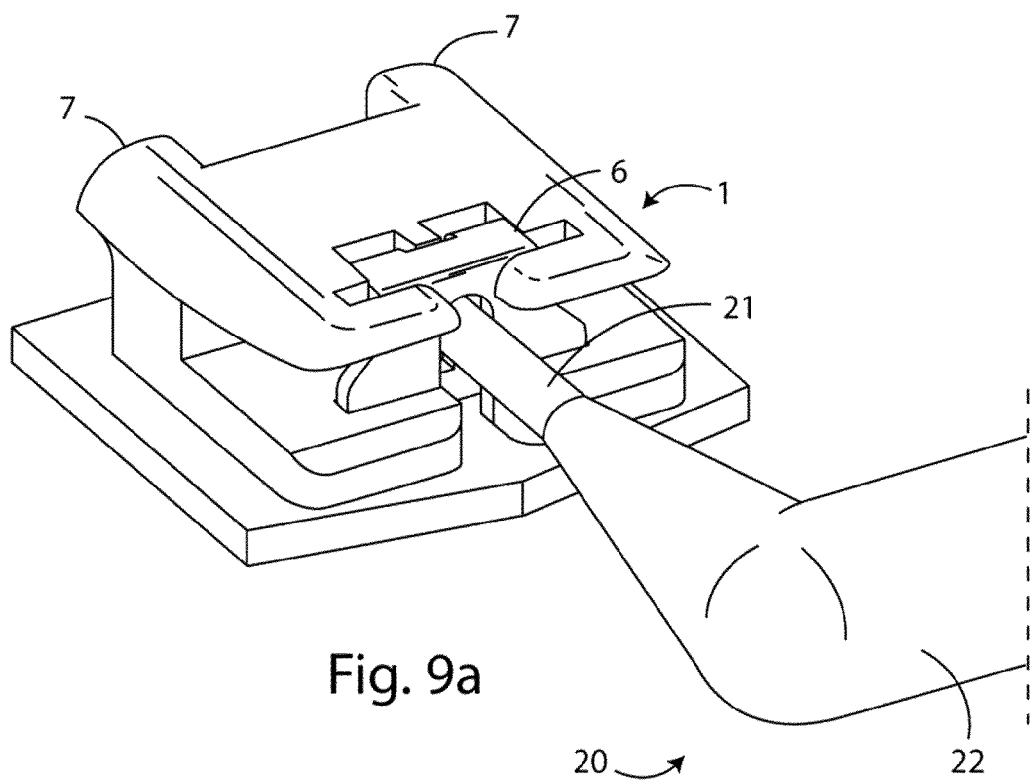
FIGS. 9a and 9b are perspective views of the device according to the invention with the opening tool.
Figure 9B:
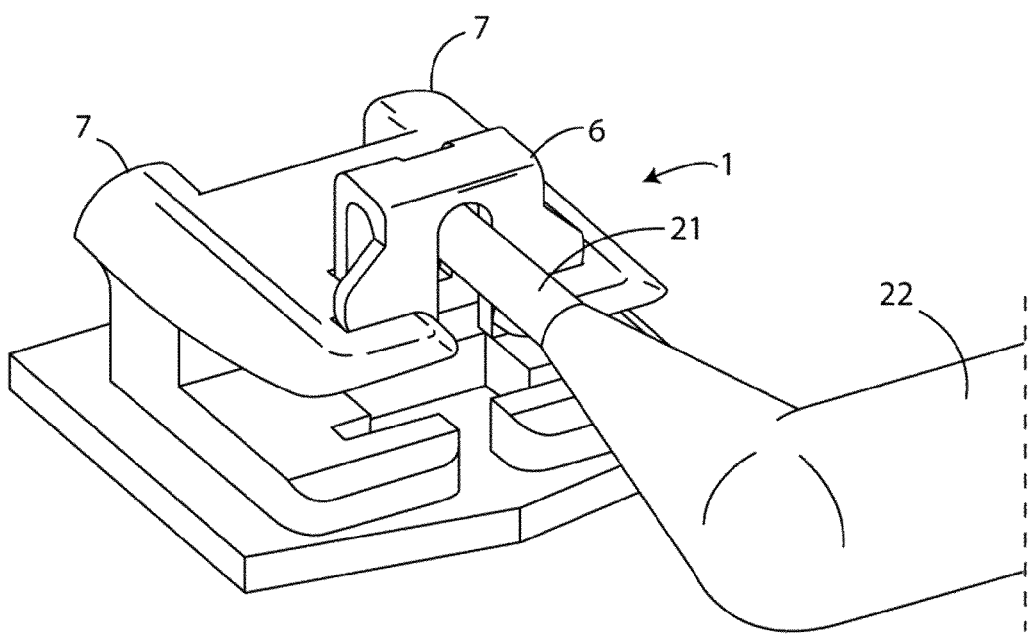
Figure 10A:
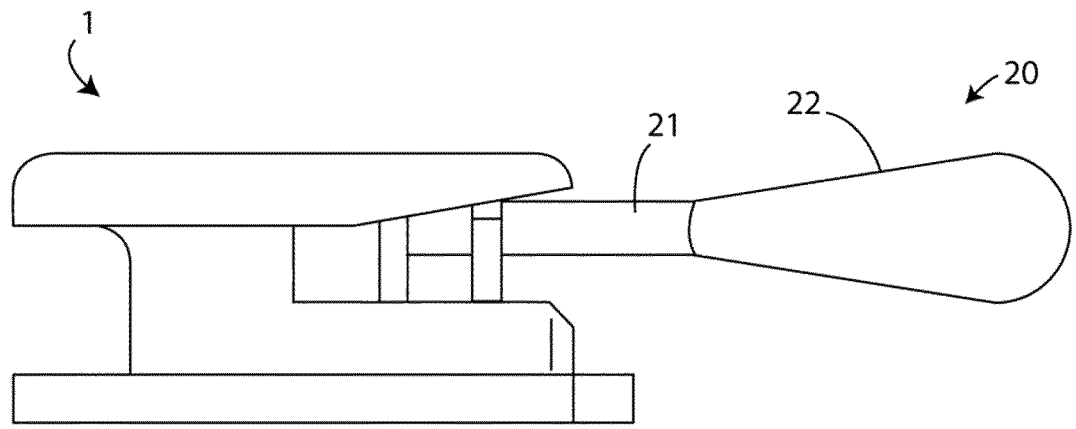
FIGS. 10a and 10b are side views of the device according to the invention with the opening tool.
Figure 10B:
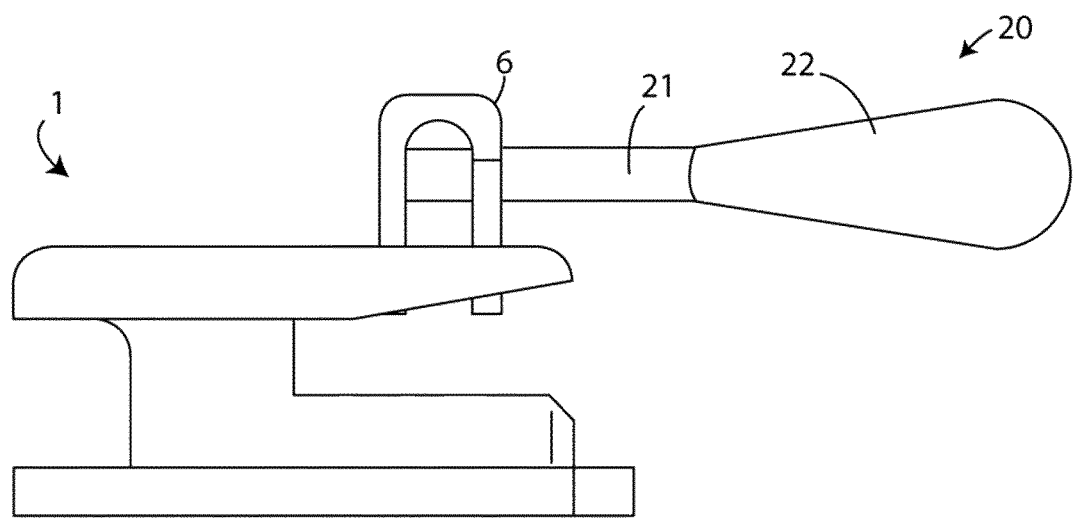

Observing now the FIGS. 9 and 10, in order to move the clip from the closing position (FIGS. 9a and 10a) to the opening position (FIGS. 9b and 10b), it is necessary a tool 20, equipped with a tip 21 suitable for coupling itself with said slit 13, and a handle 22. The tool 20 allows to exert on the clip 6 a force in the lingual-vestibular direction, enough to make the flaps 14 pass through the grooves 17 on the vestibular arm 9 of the body 3.

Figure 11A:
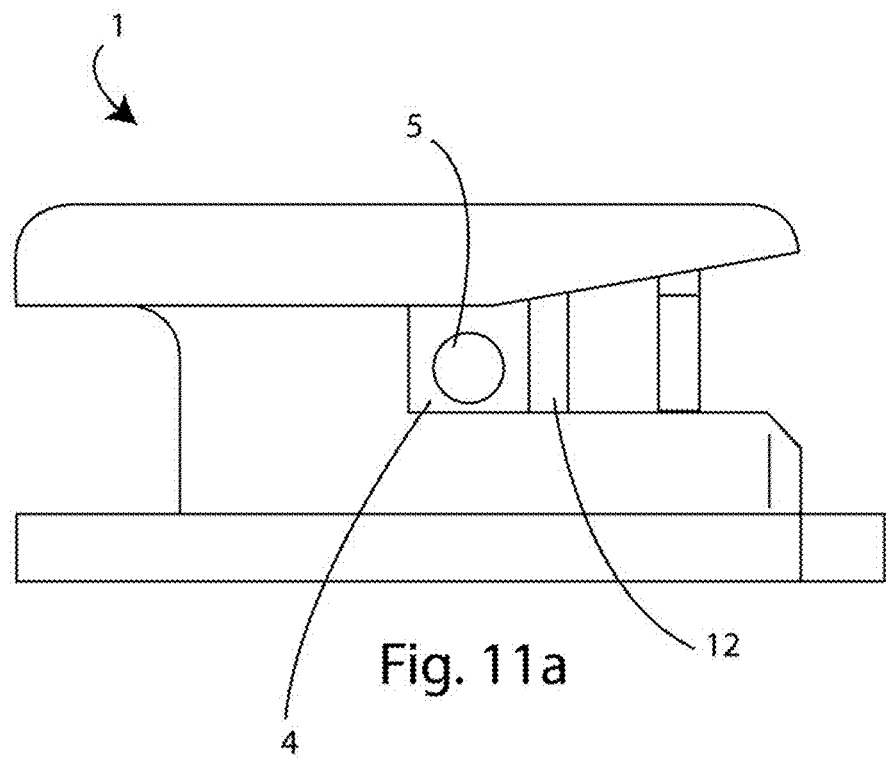
FIGS. 11a and 11b are side views of the device according to the invention, respectively during the passive and the active stages.
Figure 11B:
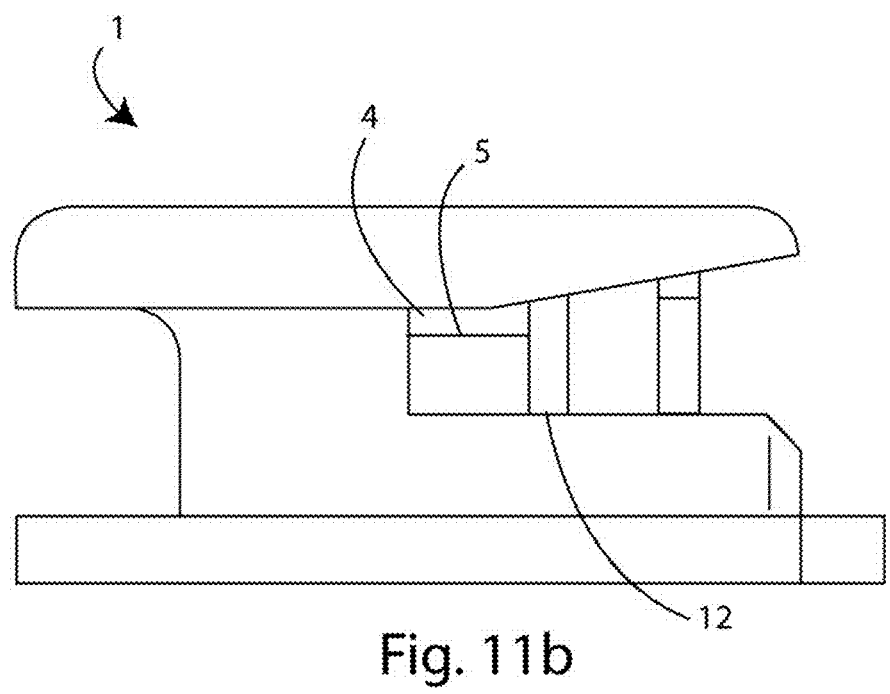

Observing now FIG. 11, it evident that the device 1 according to the invention is suitable for using an arch wire 5 with a round section (FIG. 11a) or rectangular section (FIG. 11b). In case of an arch wire 5 with a round section, the arm 12 of the clip 6 does not press the arch wire on the internal wall of the slot 4, so friction between the arm 12 of the clip 6 and the arch wire 5 is not generated (passive stage). In case of an arch wire 5 with a round section, oriented in order to place the longest side of its section along the gingival-occlusal direction, the arm 12 creates a push on the arch wire 5, pressing it on the internal wall of the slot 4 (active stage).

The "U"-shaped section of the clip 6 allows to create a force that presses constantly the arch wire 5 into the slot 4, ensuring its stability. In fact, the clip 6, tend to keep the arms 11, 12, separated from each other, so as to keep the arch wire 5 in contact with at least two internal walls of the slot 4, acquiring a sufficient rigidity to at least get the same results obtained by the known ligating devices, that use traditional arch wires with a rectangular section oriented with its longest side along the lingual-vestibular direction.

The materials, with which the device according to the present invention can be realized, can be advantageously those typical of these types of devices, which are mainly: stainless steel, titanium, nickel-titanium alloys, plastics, ceramics, alumina, zirconia, synthetic sapphire.

Figure 12:
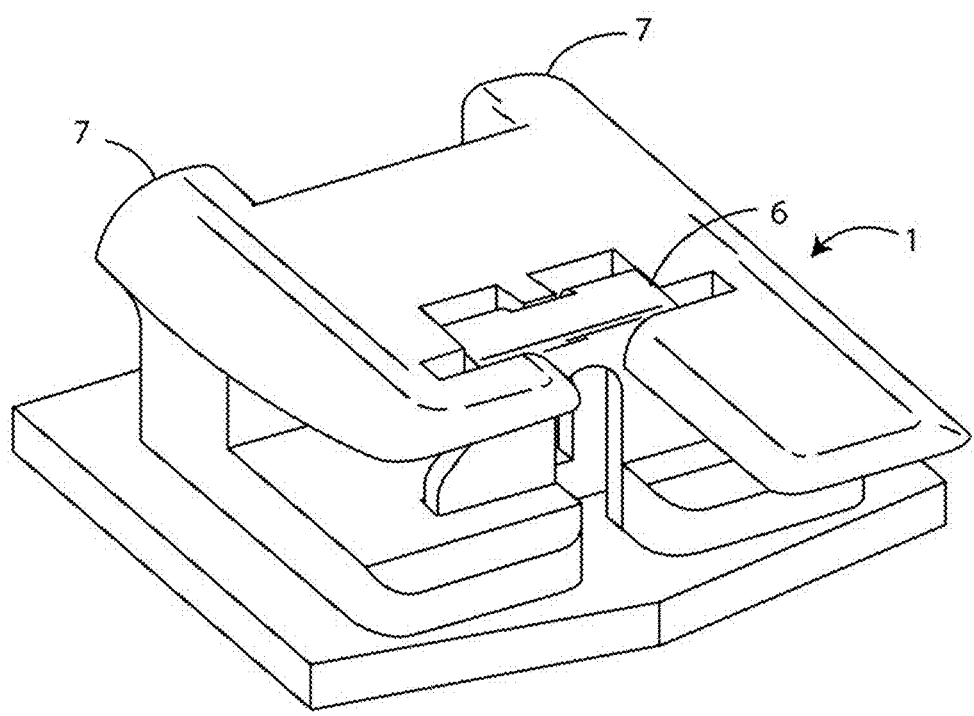
FIG. 12 is a perspective view of a third embodiment of a device according to the invention.
Figure 13:
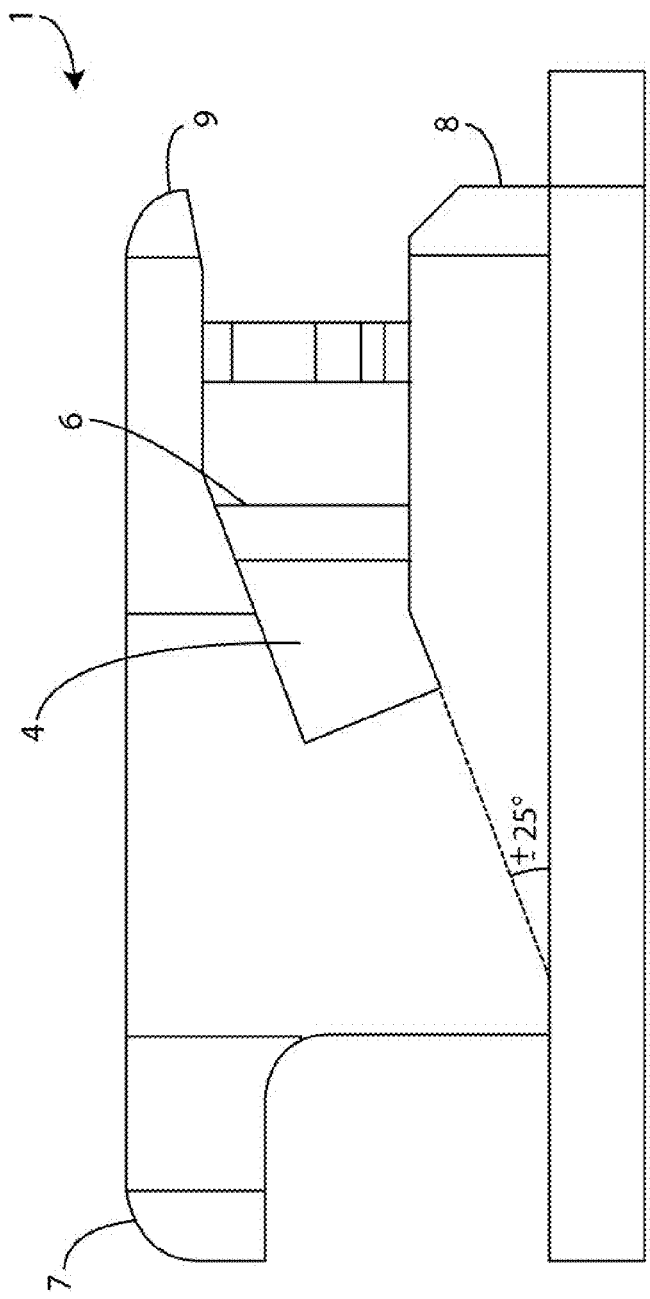
FIG. 13 is a side view of a fourth embodiment of a device according to the invention.
Figure 14:
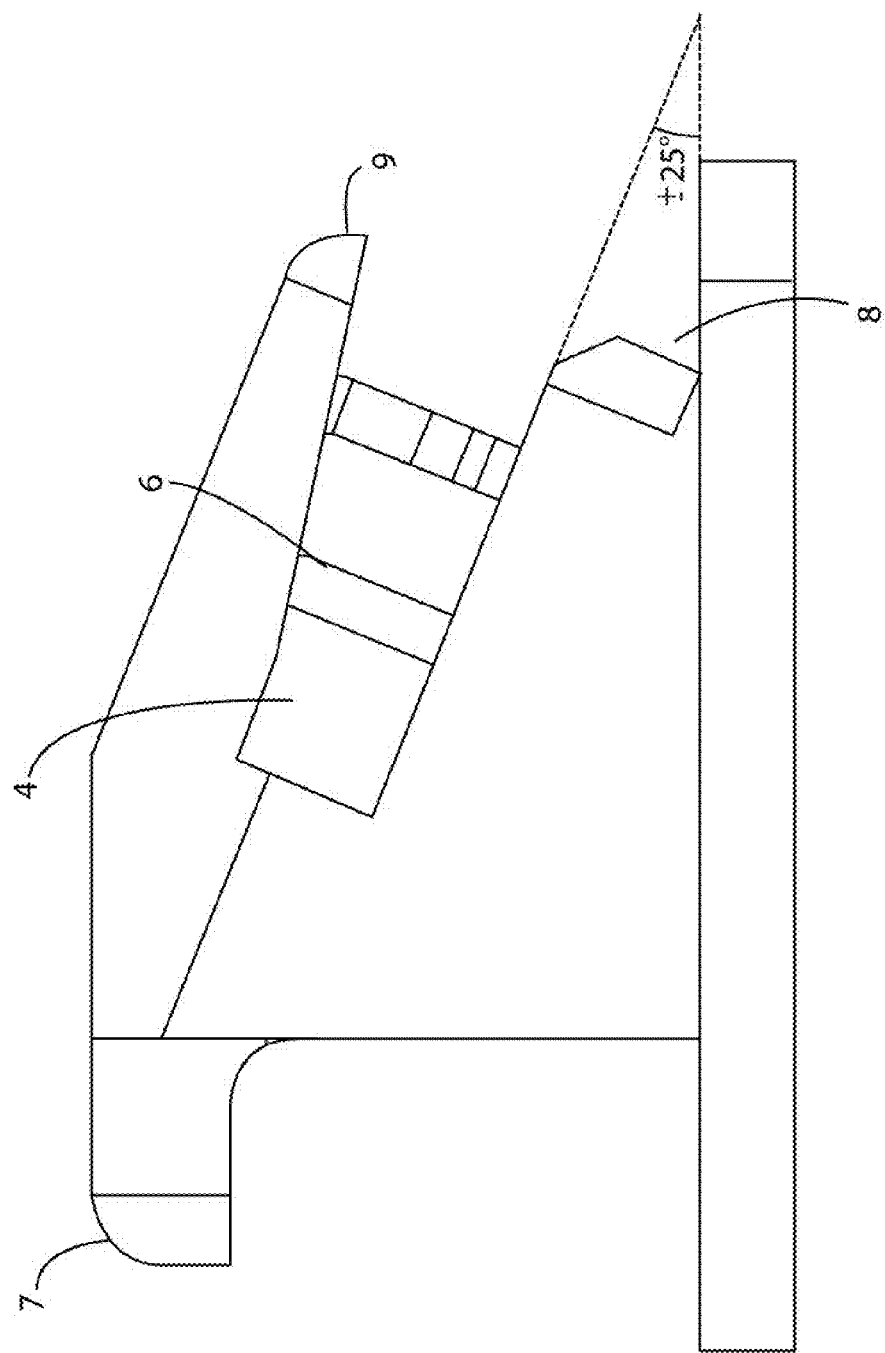
FIG. 14 is a side view of a fifth embodiment of a device according to the invention.

Advantageously, the device may or may not be equipped with hooks and/or all of bindings and the appendices that are typical of such products as hooks 23 (FIG. 12) and/or tie wings 7 and furthermore it will be equipped with all the characteristics of orthodontic brackets already known in orthodontics as "tip, torque, in-out" depending on the selected requirements (FIGS. 13 and 14).

The present invention has been described for illustrative and not limitative purposes, according to its preferred embodiments, but it is to be understood that modifications and/or changes can be introduced by those skilled in the art without departing from the relevant scope as defined in the enclosed claims.

The invention claimed is:

1. A ligating device (1) for arch wires or orthodontic wires, comprising a bondable base (2), for coupling to the tooth, and a main body (3), said main body having a slot (4), suitable for receiving a metal arch wire or orthodontic wire (5), said device (1) being characterized in that said slot (4) has an entrance on a gingival or occlusal side where said slot (4) is made accessible or closable by a clip (6; 6'), said body (3) having, along a vestibular-lingual axis, an opening (10) said opening (10) being accessible from, and being suitable for receiving said clip (6; 6'), from, the vestibular side or from outside the tooth on which the ligating device is installed and in that said clip (6; 6') opens and closes said slot (4) sliding along said vestibular-lingual axis wherein said clip (6; 6') is substantially "U"-shaped, having one first arm (11) which faces and closes or opens said entrance of said slot (4) and a second arm (12) opposite to said slot (4) with respect to the first arm (11), said first arm (11) having flaps (14) which prevent said clip from passing through grooves (17) in a vestibular arm (9) on said main body (3) said first arm (11) having a second slit (13) and said second arm (12) having a first slit (15;15').

2. The device (1) according to claim 1, characterized in that said slot (4), in case said arch wire (5) has a substantially rectangular section, is shaped such as to receive said arch wire (5) with the longest side of a section of the device which is oriented along the gingival-occlusal direction.

3. The device (1) according to claim 1, characterized in that said slot (4) has a tilt from the gingival-occlusal axis, of an angle comprised between −25° and +25°.

4. The device (1) according to claim 1, characterized in that said body (3) has, on the side opposite to said entrance of said slot (4), tie wings (7).

5. The device (1) according to claim 1, characterized in that said body (3) has, on a side of said body that abuts a gingival side, one or more hooks (23).

6. The device (1) according to claim 1, characterized in that said second arm (12) of said clip (6; 6') has a first slit (15; 15'), provided with at least an obstacle (16; 16'), next to a free end, and in that said opening (10) has, along a side, opposite to said entrance of said slot (4), in central position, a protrusion (18), suitable for guiding the sliding of said clip (6; 6') along said first slit (15; 15'), and for stopping said clip (6;6') close to said at least one obstacle (16; 16'), so that said clip (6; 6') does not come out from said body (3).

7. The device (1) according to claim 1, characterized in that said first arm (11) of said clip (6; 6') has a second slit (13), that defines two flaps (14), and in that said opening (10) has, at the end of one side, gingival or occlusal, two grooves (17), suitable for receiving said flaps (14) in one opening and/or closing stage of said device (1).

8. The device (1) according to claim 7, characterized in that said flaps (14) have a shape protruding toward outside from the total volume of said clip (6; 6').

9. The device (1) according to claim 8, characterized in that said grooves (17) have external inclined walls (19), suitable for facilitating the introduction of said clip (6; 6') with the only pressure of the fingers of a user, and for preventing said clip from coming out in the absence of an external force.

10. The device (1) according to claim 1, characterized in that said device is adapted to allow the use of an external tool (20), equipped with a handle (22) and a tip (21), suitable for coupling said external tool (20) with a first slit (13), in order to exert on a clip (6; 6') a force in the lingual-vestibular direction that causes flaps (14) to move closer to each other to compress said first slit (13), where said force is sufficient to make said slot (4) move from a closed position to an open position.

11. A ligating device (1) for arch wires or orthodontic wires, comprising a bondable base (2), for coupling to the tooth, and a main body (3), said main body having a slot (4), suitable for receiving a metal arch wire or orthodontic wire (5), said device (1) being characterized in that said slot (4) has an entrance on a gingival or occlusal side where said slot (4) is made accessible or closable by a clip (6; 6'), said body (3) having on the plane parallel to the tooth on which the device installed, an opening (10), suitable for receiving said clip (6; 6'), wherein said body (3) has a substantially "U"-shaped section, defined on both sides of said slot (4) by a first lingual arm (8) and a second vestibular arm (9) and in that said clip (6; 6') opens and closes said slot (4) sliding along a vestibular-lingual axis wherein said clip (6; 6') is substantially "U"-shaped, having one first arm (11) which faces and closes or opens said entrance of said slot (4) and a second arm (12) opposite to said first arm (11), said first arm (11) having flaps (14) which prevent said clip from passing through grooves (17) of said second vestibular arm (9), said first arm having a second slit (13) and said second arm having a first slit (15;15') wherein said device is adapted to allow the use of an external tool (20), equipped with a handle (22) and a tip (21), suitable for coupling itself with a first slit (13), in order to exert on a clip (6; 6') a force in the lingual-vestibular direction, where said force is sufficient to make said slot (4) move from a closed position to an open position.

* * * * *